(12) United States Patent
Termyna et al.

(10) Patent No.: US 9,504,495 B2
(45) Date of Patent: Nov. 29, 2016

(54) MULTI-AXIAL PEDICLE FIXATION ASSEMBLY AND METHOD FOR USE

(75) Inventors: Stephen Termyna, Boonton, NJ (US); John Lovell, North Bergen, NJ (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 537 days.

(21) Appl. No.: 13/026,204

(22) Filed: Feb. 11, 2011

(65) Prior Publication Data

US 2012/0209335 A1   Aug. 16, 2012

(51) Int. Cl.
*A61B 17/70*   (2006.01)

(52) U.S. Cl.
CPC .................... *A61B 17/7037* (2013.01)

(58) Field of Classification Search
CPC .......... A61B 17/7037; B25B 23/0028; B25B 23/0035; B25B 23/0042
USPC ......... 606/305–308, 319, 325, 328, 264–272
See application file for complete search history.

(56) References Cited

U.S. PATENT DOCUMENTS

| | | | |
|---|---|---|---|
| 4,065,941 A | 1/1978 | Aoki | |
| 5,509,331 A * | 4/1996 | Nickipuck | 81/58.3 |
| 5,630,342 A * | 5/1997 | Owoc | 81/57.39 |
| 5,687,623 A * | 11/1997 | Hsieh | 81/60 |
| 5,800,435 A | 9/1998 | Errico et al. | |
| 6,485,494 B1 | 11/2002 | Haider | |
| 6,554,834 B1 * | 4/2003 | Crozet et al. | 606/65 |
| 6,565,567 B1 | 5/2003 | Haider | |
| 6,974,460 B2 | 12/2005 | Carbone et al. | |
| 7,087,057 B2 | 8/2006 | Konieczynski et al. | |
| 7,163,539 B2 | 1/2007 | Abdelgany et al. | |
| 7,559,943 B2 | 7/2009 | Mujwid | |
| 7,776,067 B2 | 8/2010 | Jackson | |
| 8,021,398 B2 * | 9/2011 | Sweeney et al. | 606/269 |
| 8,998,963 B2 * | 4/2015 | Ziolo et al. | 606/289 |
| 2004/0056345 A1 * | 3/2004 | Gilleo | 257/698 |
| 2004/0254577 A1 | 12/2004 | Delecrin et al. | |
| 2005/0010215 A1 | 1/2005 | Delecrin | |
| 2006/0129149 A1 * | 6/2006 | Iott et al. | 606/61 |
| 2006/0241603 A1 * | 10/2006 | Jackson | 606/61 |
| 2006/0276789 A1 | 12/2006 | Jackson | |
| 2007/0093846 A1 * | 4/2007 | Frigg et al. | 606/90 |
| 2008/0077139 A1 | 3/2008 | Landry et al. | |
| 2008/0287998 A1 | 11/2008 | Doubler et al. | |
| 2008/0312692 A1 * | 12/2008 | Brennan et al. | 606/246 |
| 2009/0163961 A1 * | 6/2009 | Kirschman | 606/301 |

(Continued)

OTHER PUBLICATIONS

PCT/US2012/023413, International Search Report and Written Opinion, dated May 29, 2012, 6 pages.

*Primary Examiner* — Jan Christopher Merene
*Assistant Examiner* — Atiya Mahmud
(74) *Attorney, Agent, or Firm* — Baker & McKenzie LLP

(57) ABSTRACT

An implantable orthopedic assembly comprises a bone fixator and head assembly for securing a stabilizing rod to the spine. The head assembly allows multi-axial repositioning of the bone fixator relative to the head assembly. A primary drive interface located on the bone fixator may be used to adjust the depth of bone penetration when the bone fixator and head assembly are substantially coaxial. A secondary drive interface located on the head assembly may be used to adjust the depth of bone penetration while independently adjusting the stabilizing rod position when the bone fixator and the head assembly are not coaxial, transferring torsional loads to the bone fixator.

19 Claims, 18 Drawing Sheets

(56) References Cited

U.S. PATENT DOCUMENTS

| | | |
|---|---|---|
| 2010/0036417 A1 | 2/2010 | James et al. |
| 2010/0125302 A1 | 5/2010 | Hammill, Sr. et al. |
| 2010/0137920 A1 | 6/2010 | Hammill, Sr. et al. |
| 2010/0160977 A1 | 6/2010 | Gephart et al. |
| 2010/0191290 A1 | 7/2010 | Felix |
| 2010/0204733 A1 | 8/2010 | Rathbun et al. |
| 2010/0204735 A1 | 8/2010 | Gephart et al. |
| 2011/0040338 A1* | 2/2011 | Jackson ............... 606/305 |
| 2011/0077694 A1* | 3/2011 | Biedermann et al. ...... 606/305 |
| 2011/0208248 A1* | 8/2011 | Barrus et al. ........... 606/305 |
| 2011/0256938 A1* | 10/2011 | Chen ................... 464/141 |
| 2012/0185003 A1* | 7/2012 | Biedermann et al. ...... 606/328 |
| 2012/0290010 A1* | 11/2012 | Zamani et al. ........... 606/264 |

* cited by examiner

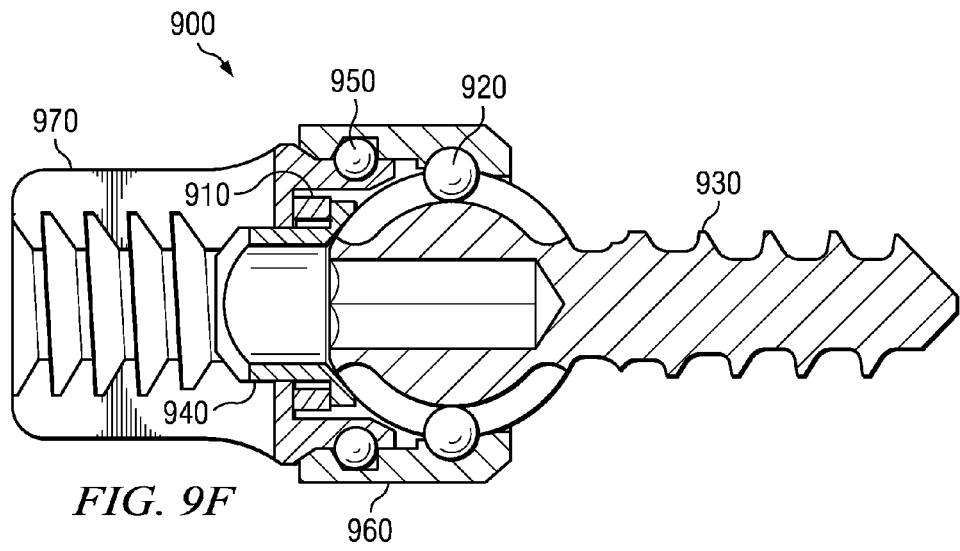
FIG. 9F
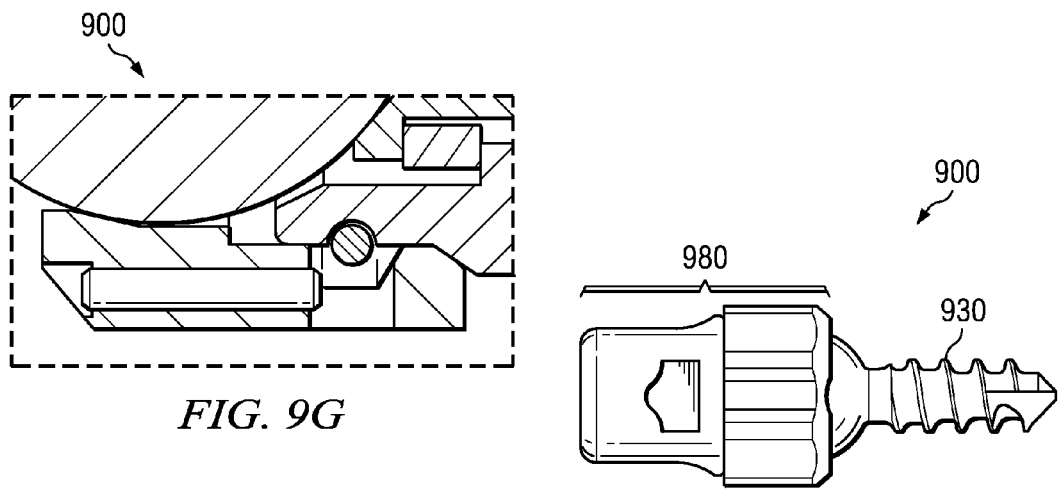
FIG. 9G
FIG. 9H
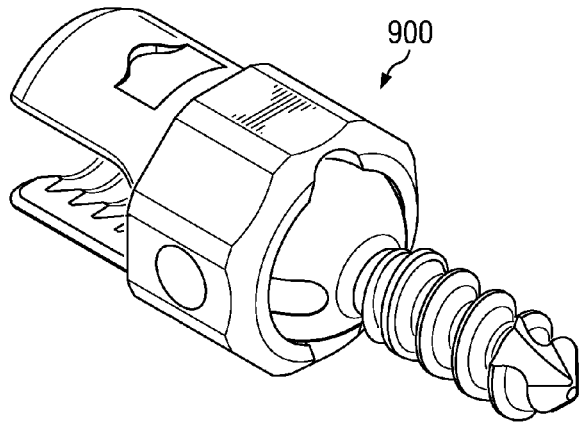
FIG. 9I

MULTI-AXIAL PEDICLE FIXATION ASSEMBLY AND METHOD FOR USE

TECHNICAL FIELD

The disclosed embodiments relate generally to orthopedic implantable device technology, and more specifically to implantable devices for use in stabilizing the spine, including devices that penetrate the vertebral pedicle, lateral mass, or transverse process.

BACKGROUND

Spinal fixation devices may be surgically implanted in the body to effect a desired relationship between adjacent vertebral bodies. Such devices typically include a rigid stabilizing rod coupled to one or more devices for anchoring the rod to the vertebral bodies. The stabilizing rod must be contoured to accommodate variations in patient anatomy as well as variations in desired therapeutic benefits. Since each vertebral body varies in size and shape, a variety of anchoring devices have been developed. Pedicle screws have a shape and size appropriate for engaging pedicle bone. Using implantable multi-axial pedicle fixation systems known in the art, surgeons may be challenged to obtain optimal bone purchase while obtaining optimal stabilizing rod position.

A need exists for an implantable multi-axial pedicle fixation system with a primary coaxial drive feature that maximizes driver interface while minimizing the bone fixator geometry required to withstand functional loading, thus increasing the degree of total multi-axial angulation available, and with a secondary non-coaxial drive feature that transfers the torsional loads required to advance or retract the bone fixator from the vertebral pedicle, lateral mass, or transverse process.

BRIEF SUMMARY

Disclosed herein are various embodiments of an implantable orthopedic assembly generally comprising a bone fixator and a head assembly. Embodiments of the bone fixator may be comprised of a substantially spherical knob having two opposing longitudinally elongated apertures, such as hemispherical blind apertures, and a longitudinally elongated shaft, such as a screw shaft, extending outwardly from the knob. The head assembly is generally cross-linked to the bone fixator via spherical balls positioned within the elongated apertures on the knob of the bone fixator. In alternate embodiments, the head assembly may be cross-linked to the bone fixator via hinge pins or other suitable devices.

Embodiments of the head assembly may comprise a body component coaxially connected to a secondary drive component, such that the body component may be rotationally repositioned relative to the secondary drive component. The body component may comprise a channel configured to receive a stabilizing rod. Embodiments of the head assembly may further comprise an internal saddle member adapted to transfer a received load from the stabilizing rod to the bone fixator. A pre-loading component, such as a wave spring, may exert a pre-load on the internal saddle member. Embodiments of the head assembly may be adapted to allow multi-axial repositioning of the bone fixator relative to the head assembly, and are generally adapted to transfer torsional loads to the bone fixator. In some embodiments, the body component may comprise a split body connected to the secondary drive component with a press fit.

Embodiments of the bone fixator may comprise a primary drive interface, such as a hex or other interface accessible through the head assembly or an elongated drive post extending from the knob through the head assembly. The elongated drive post may be configured to break away from the knob. Embodiments of the secondary drive component may comprise a secondary drive interface, such as a square, a hex, an octagon, or other interface.

Also disclosed herein are various embodiments of a method of constructing an implantable orthopedic assembly as described above. The method may comprise positioning first and second spherical balls within first and second receptacles on the head assembly drive component, inserting the bone fixator through the drive component, arranging the positioned spherical balls within the elongated apertures of the bone fixator knob, positioning the internal saddle member within the head assembly body component, coaxially uniting the drive component with the body component such that the internal saddle member contacts the bone fixator, and securing the body component to the drive component such that the secured body component is rotationally repositionable relative to the drive component. Embodiments may also comprise positioning a pre-loading component, such as a wave spring, between the internal saddle member and the body component to exert a pre-load on the internal saddle member.

Securing the body component to the drive component may comprise aligning fastening ball dimples located on the body component with an opening on the drive component and inserting fastening balls into the dimples. Alternatively, securing the body component to the drive component may comprise aligning fastening pin receptacles located on the drive component with a fastening pin channel located on the body component and inserting fastening pins into the receptacles.

Also disclosed herein are various embodiments of a method of adjusting bone penetration depth of an implantable orthopedic assembly as described above. The method generally comprises fixating the bone fixator into bone, multi-axially repositioning the head assembly relative to the bone fixator until the desired position is achieved, and securing a stabilizing rod in a body component of the head assembly, such that further repositioning of the head assembly is prevented. Some embodiments may also comprise rotationally repositioning the body component of the head assembly relative to a drive component of the head assembly prior to securing the stabilizing rod. After the stabilizing rod is secured, and without removing or further adjusting the stabilizing rod, the drive component of the head assembly may then be adjusted, for example with a tool interfaced with the drive component. Such adjusting of the drive component results in the transfer of a torsional load to the bone fixator, causing the bone fixator to advance into the bone or retract from the bone.

BRIEF DESCRIPTION OF THE DRAWINGS

FIGS. 9A through 9I illustrate various views of an embodiment of an implantable multi-axial pedicle fixation assembly.

DETAILED DESCRIPTION

Figure 1A:
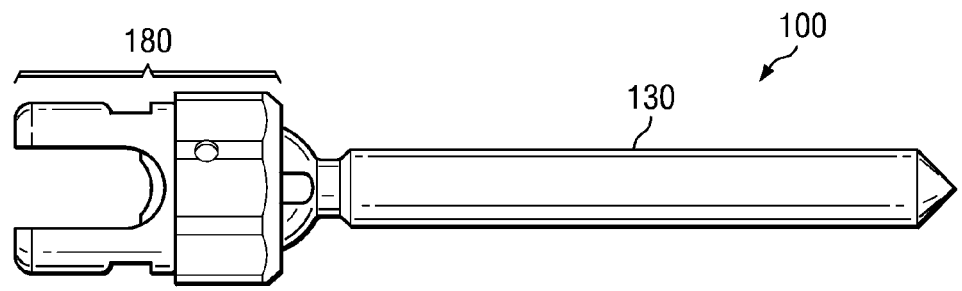
FIGS. 1A through 1G illustrate various views of an embodiment of an implantable multi-axial pedicle fixation assembly.
Figure 1B:
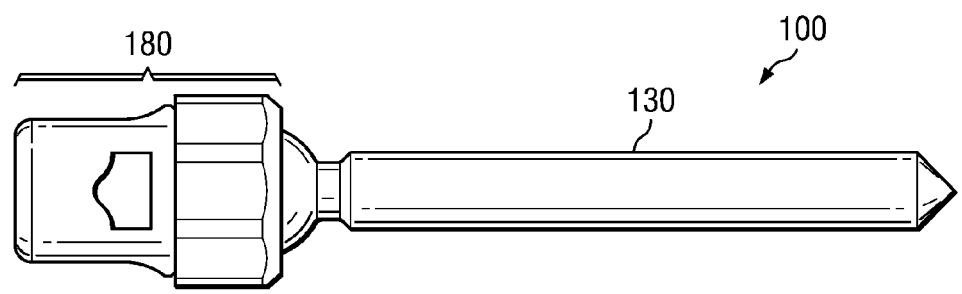
Figure 1C:
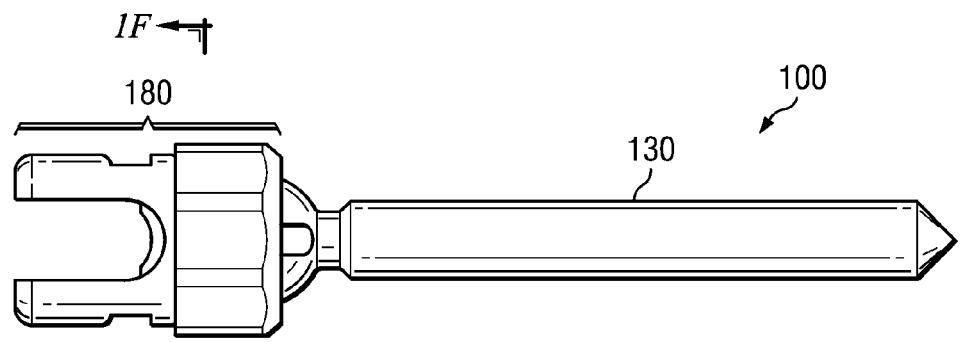
Figure 1D:
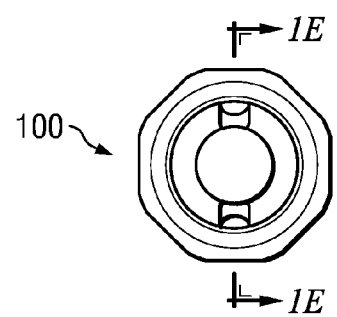
Figure 1E:
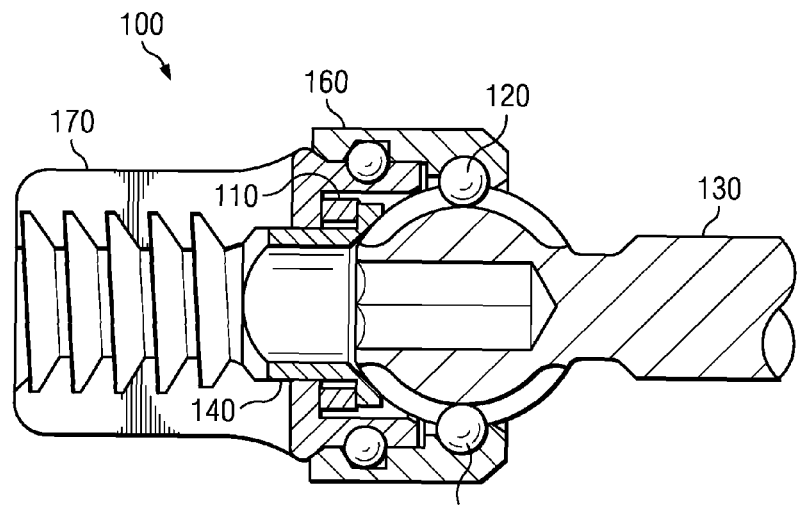
Figure 1F:
Figure 1G:
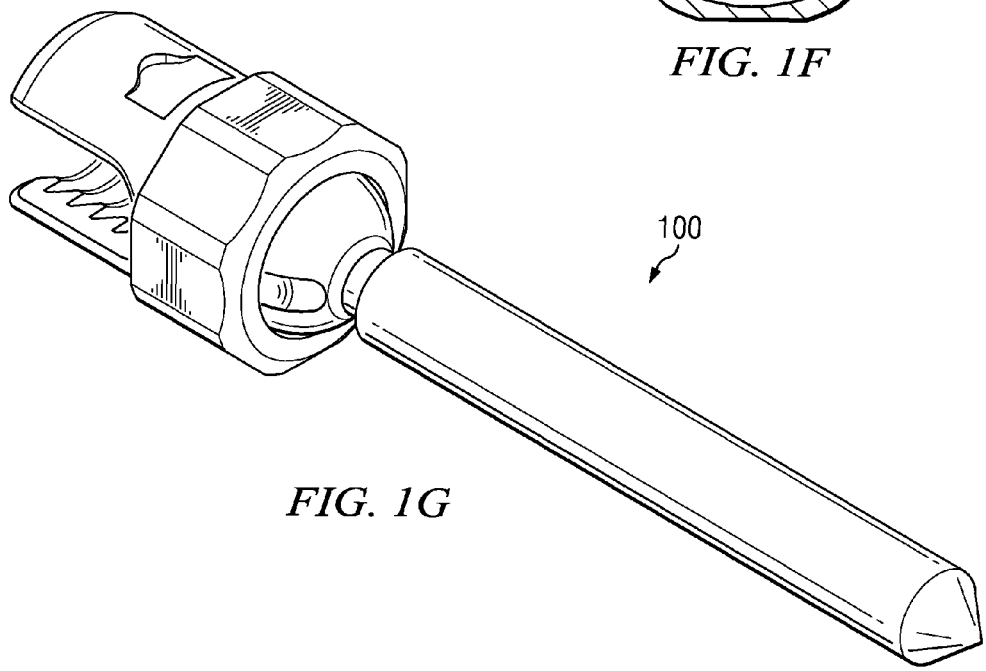

Various views of an exemplary embodiment of an implantable multi-axial pedicle fixation assembly 100 are illustrated in FIGS. 1A through 1G. Bone fixator 130 is angulatably connected to head assembly 180 such that the axis of bone fixator 130 may pivot relative to the axis of head assembly 180. Among other desirable benefits, this multi-axial feature maximizes range of motion and minimizes the need for extensive contouring of a spine stabilizing rod secured by head assembly 180, and also provides for simplified customization to accommodate variations in patient anatomy as well as variations in desired therapeutic benefits.

When the axis of bone fixator 130 and the axis of head assembly 180 are relatively aligned, such as during initial implantation, a primary drive interface may be used to adjust the depth at which bone fixator 130 penetrates the bone. The primary drive interface is located on bone fixator 130 and may be accessed with a tool inserted through head assembly 180. In embodiments not shown, the primary drive interface may be a post integral with bone fixator 130 that extends through head assembly 180. In such embodiments, the post may attach to a tool specially adapted to secure and drive the implant, and the post may have a break-off feature so that the post may be removed after initial implantation. Such break-off features may be designed to break below the point of contact between bone fixator 130 and head assembly 180 to ensure a consistent contact surface.

Head assembly 180 comprises secondary drive component 160 and body component 170. Head assembly body component 170 is configured with a channel for receiving a spine stabilizing rod. Internal saddle member 140, for example a pressure cap, may nest within head assembly body component 170 and contact the stabilizing rod. When a stabilizing rod is secured within the channel of head assembly body component 170 with, for example, a setscrew or other such blocker, internal saddle member 140 transfers the received load to bone fixator 130, thus securing both the stabilizing rod and bone fixator 130 simultaneously. Wave spring 110 may place a pre-load upon the locking mechanism, such as a 2.5-4.0 lb. pre-load. Some embodiments may pre-load the locking mechanism with greater or lesser force. Other embodiments may use a different system or no system for pre-loading the locking mechanism. In embodiments not shown, two integral cantilever springs within internal saddle member 140 may place a pre-load upon the locking mechanism. For ease of assembly, the pins that deflect the cantilever springs may be notched such that there is clearance from the spring surface upon insertion. Once the pins are placed, they may be turned 180 degrees to make contact with the spring and thus generate the pre-load.

A secondary drive feature may operate similarly to a universal joint in that a kinematic linkage may be used to connect two angularly misaligned components, such as head assembly 180 and bone fixator 130. Since head assembly body component 170 is rotatably connected to head assembly secondary drive component 160 such that these components can rotate independently of one another, the rod-receiving channel of head assembly body component 170 may be independently repositioned while adjusting the depth at which bone fixator 130 penetrates the bone via the head assembly secondary drive component 160. Head assembly secondary drive component 160 may be cross-linked to bone fixator 130 via spherical drive balls 120. Spherical drive balls 120, which do not receive a locking load, traverse bone fixator 130 along elongated apertures, thus allowing multi-axial movement of head assembly 180 while transferring torsional loads to bone fixator 130. Such torsional loads adjust the depth at which bone fixator 130 penetrates the bone. Torsional loads may be applied to the secondary drive component regardless of multi-axial mechanism position. In embodiments not shown, head assembly secondary drive component 160 may be cross-linked to bone fixator 130 via hinge pins or any other construct suitable to traverse bone fixator 130 along elongated apertures, thus allowing multi-axial movement of head assembly 180 while transferring torsional loads to bone fixator 130. The drive interface for head assembly secondary drive component 160 may be a square drive, a hex, an octagon, a spline, a gear, or any other suitable drive interface, and may require the use of an external tool to adjust the depth of bone penetration.

The depth at which the bone fixator penetrates the bone may be adjusted using the secondary drive feature prior to insertion of a stabilizing rod in the head assembly. The depth may also be adjusted after insertion of a stabilizing rod, eliminating the need to remove the rod before adjusting the bone fixator. This provides a clear benefit to the surgeon, because an imperfectly contoured stabilizing rod will no longer need to be removed for re-contouring or bone fixator repositioning; instead, the secondary drive feature speeds up the process by allowing the surgeon to adjust screw height with the stabilizing rod in place.

Figure 2A:
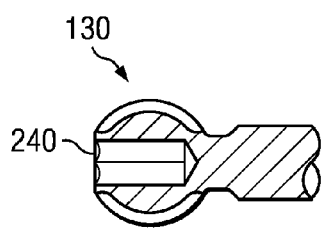
FIGS. 2A through 2D illustrate various views of an embodiment of a bone fixator component of an implantable multi-axial pedicle fixation assembly.
Figure 2B:
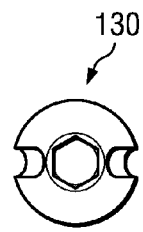
Figure 2D:
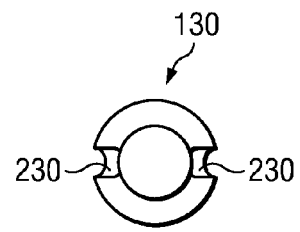
Figure 2C:
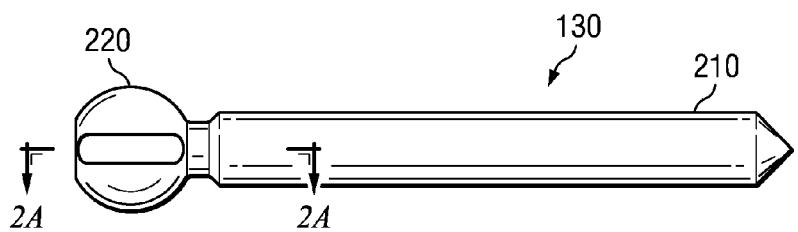

Various views of an exemplary embodiment of a bone fixator component 130 are illustrated in FIGS. 2A through 2D. Bone fixator 130 may be of any size and shape appropriate for penetrating a vertebral pedicle bone, may be solid, hollow, or a combination of solid and hollow, and may be made from any material suitable for implantation into the body, such as stainless steel, titanium, ceramic, cobalt chromium, or a composite material. Shaft 210 may be smooth, or may be roughened, scored, or otherwise textured, and may generally be configured as a nail, a screw, a pin, or any other configuration suitable for bone fixation. Shaft 210 may be cross-sectionally circular, polygonal, or any other shape suitable for bone fixation, and its bone-engaging terminus may be pointed, rounded, flattened, or otherwise shaped in a suitable manner for bone fixation. Knob 220 may be integral with shaft 210 or may be a separate component rigidly coupled to shaft 210. The surface of knob 220 may be spherical, and two elongated apertures 230 may be diametrically opposed on either side of knob 220. In this embodiment, elongated apertures 230 are hemispherical blind apertures, such that spherical drive ball 120 (see FIG. 1) can roll smoothly along the aperture. In embodiments not shown, elongated apertures 230 and drive ball 120 may be otherwise configured as long as drive ball 120 can traverse the aperture, for example, drive ball 120 may be non-spherical. Primary drive interface 240 is located on knob 220 opposite shaft 210. In the embodiment shown, primary drive interface 240 is a hex screwdriver interface accessed with a tool (not shown), though other suitable primary drive interfaces are contemplated.

Figure 3A:
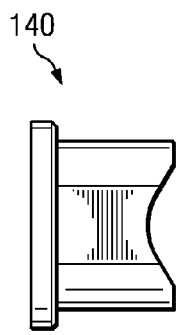
FIGS. 3A through 3E illustrate various views of an embodiment of an internal saddle member of an implantable multi-axial pedicle fixation assembly.
Figure 3B:
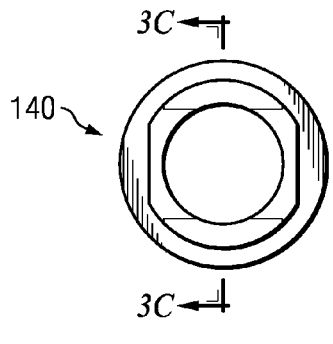
Figure 3C:
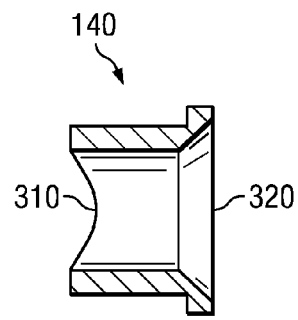
Figure 3D:
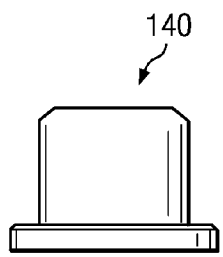
Figure 3E:
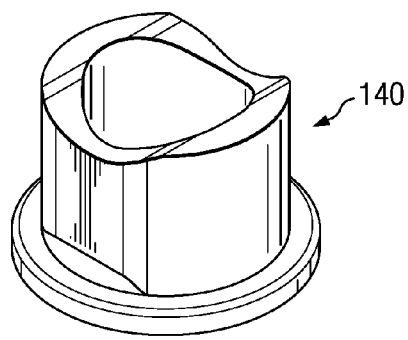

Various views of an exemplary embodiment of an internal saddle member 140 are illustrated in FIGS. 3A through 3E. Internal saddle member 140 may be positioned within a receptacle of head assembly body component 170 (see FIG. 1) such that rod-receiving channel 310 aligns with the rod-receiving channel of head assembly body component 170. Internal saddle member 140 may be keyed to ensure alignment with rod-receiving channel 310. Opening 320 may be positioned to contact bone fixator 130 (see FIG. 1).

Figure 4A:
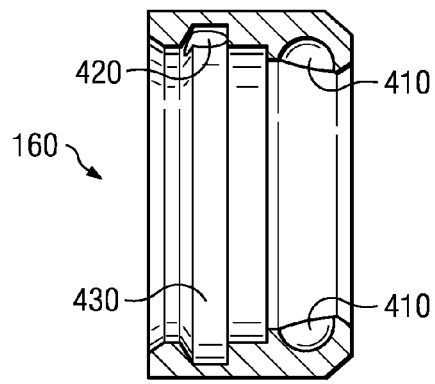
FIGS. 4A through 4F illustrate various views of an embodiment of a secondary drive component of a head assembly component of an implantable multi-axial pedicle fixation assembly.
Figure 4B:
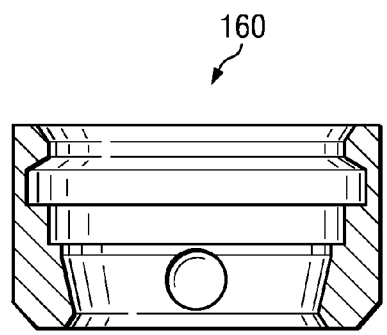
Figure 4C:
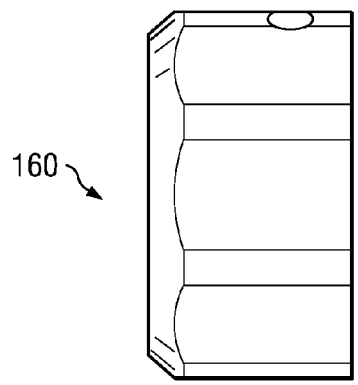
Figure 4D:
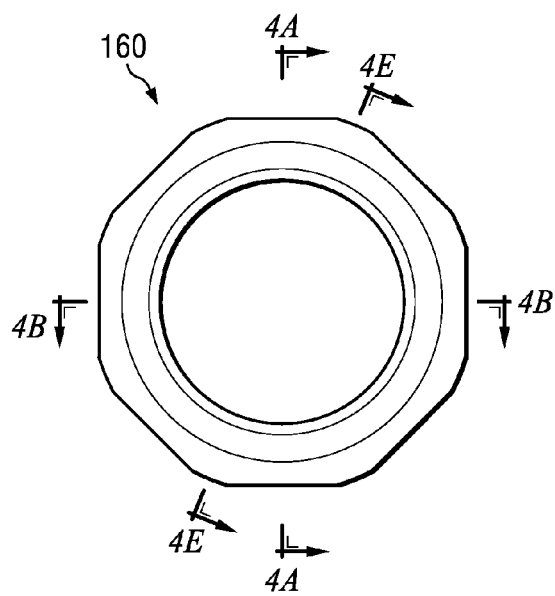
Figure 4E:
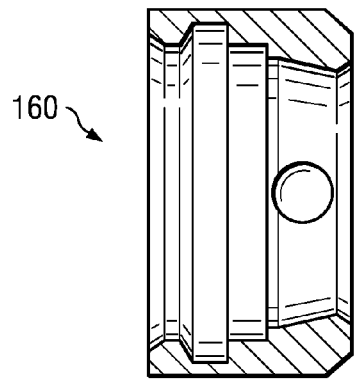
Figure 4F:
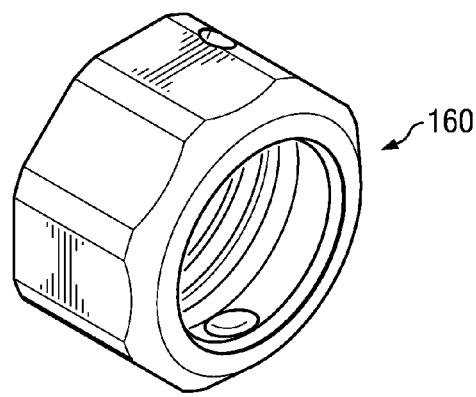
Figure 5A:
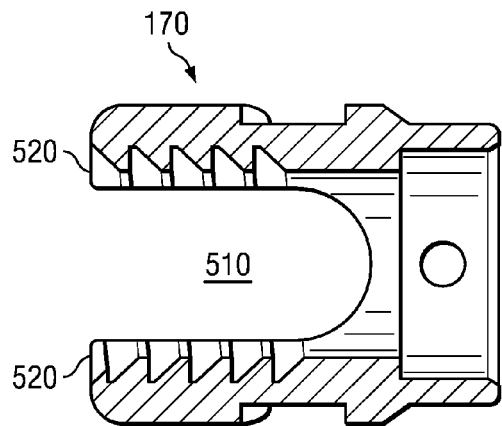
FIGS. 5A through 5I illustrate various views of an embodiment of a body component of a head assembly component of an implantable multi-axial pedicle fixation assembly.
Figure 5B:
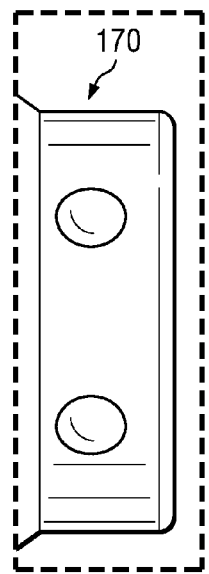
Figure 5C:
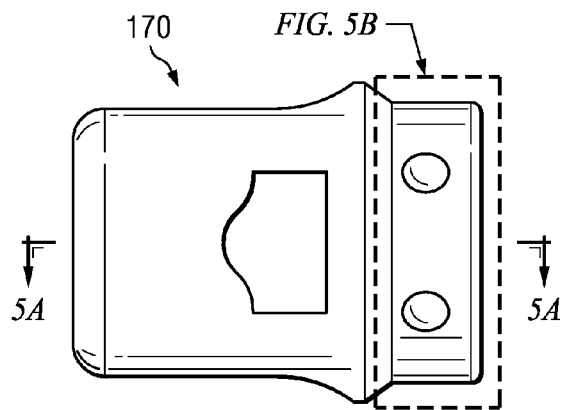
Figure 5D:
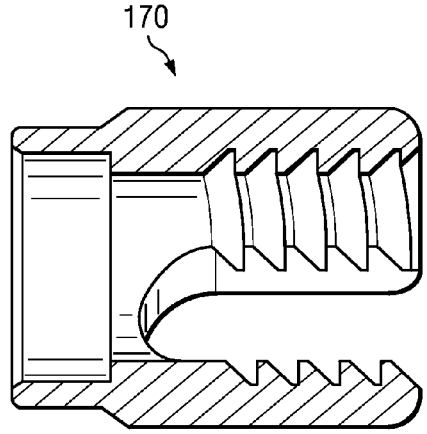
Figure 5E:
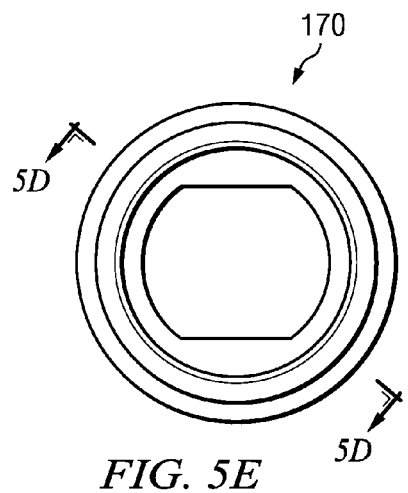
Figure 5F:
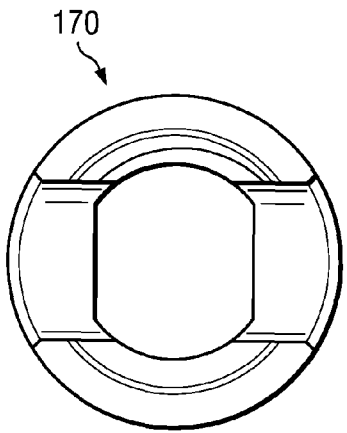
Figure 5G:
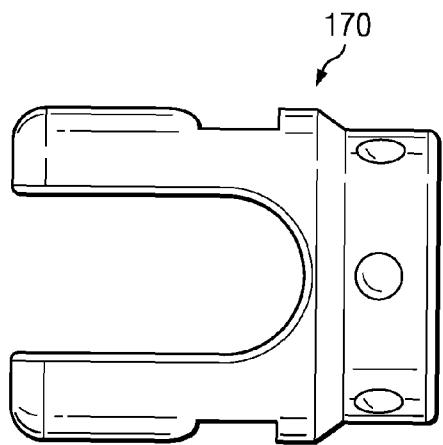
Figure 5H:
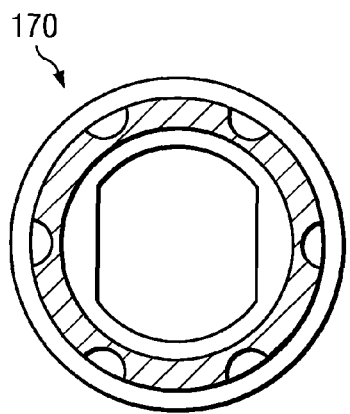
Figure 5I:
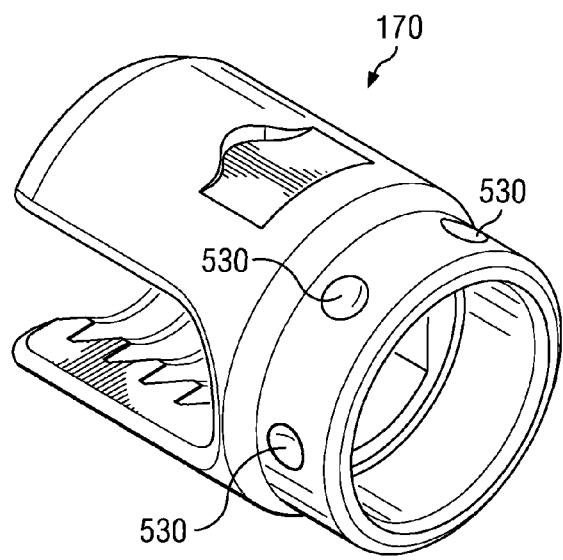

Various views of an exemplary embodiment of a head assembly secondary drive component 160 are illustrated in FIGS. 4A through 4F. Head assembly secondary drive component 160 comprises spherical drive ball receptacles 410 and opening 420 into fastening ball channel 430. Various views of an exemplary embodiment of a head assembly body component 170 are illustrated in FIGS. 5A through 5I. Head assembly body component 170 comprises rod-receiving channel 510, locking threads 520, and fastening ball dimples 530. Locking threads 520 prevent the stabilizing rod from exiting channel 510, and in some embodiments a locking nut, locking cap, setscrew, or other component (not shown) may be employed to secure the stabilizing rod in channel 510. In some embodiments, head assembly 180 is still fully or partially adjustable after the introduction of the stabilizing rod but before the stabilizing rod is fully secured.

Looking now at FIGS. 1A through 1G, 2A through 2D, 3A through 3E, 4A through 4F, and 5A through 5I, to construct an embodiment of head assembly 180, spherical drive balls 120 are inserted into spherical drive ball receptacles 410. Bone fixator 130 is then inserted through head assembly drive component 160 such that spherical drive balls 120 rest within elongated apertures 230. Internal saddle member 140 and wave spring 110 may be positioned within a receptacle of head assembly body component 170. Body component 170 may then be united with secondary drive component 160. Fastening ball dimple 530 may then be aligned with opening 420 of head assembly secondary drive component 160 for insertion of fastening ball 150 into fastening ball channel 430. Body component 170 may then be rotated until the next fastening ball dimple 530 is aligned with opening 420 for insertion of another fastening ball 150 until each fastening ball dimple 530 is occupied by a fastening ball 150, thus securing together head assembly body component 170 and head assembly secondary drive component 160, while allowing the two components to freely rotate with respect to each other. Note that in alternate embodiments, the fastening ball channel may be located on the head assembly body component, while the fastening ball dimples may be located on the head assembly drive component. In alternate embodiments not shown, the head assembly body component may be designed with a split body, such that the split body is compressed and inserted into the head assembly drive component and secured with an annular ring on the body component engaging an undercut on the drive component.

Figure 6A:
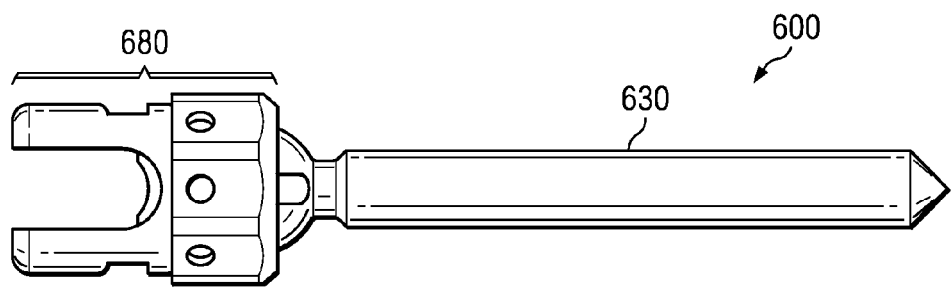
FIGS. 6A through 6F illustrate various views of an embodiment of an implantable multi-axial pedicle fixation assembly.
Figure 6B:
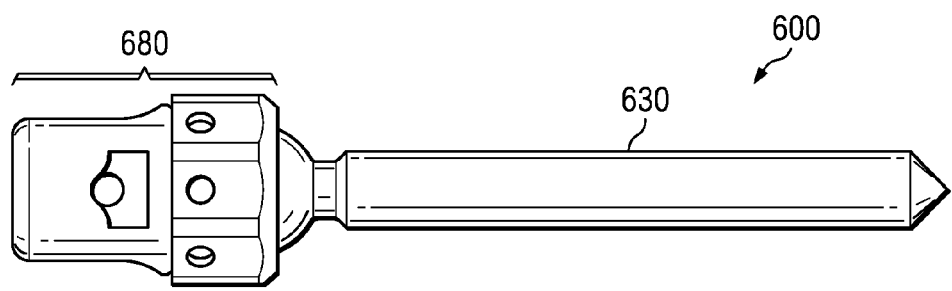
Figure 6C:
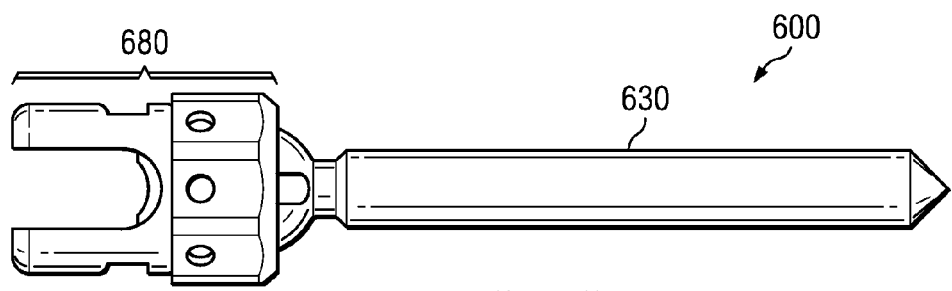
Figure 6D:
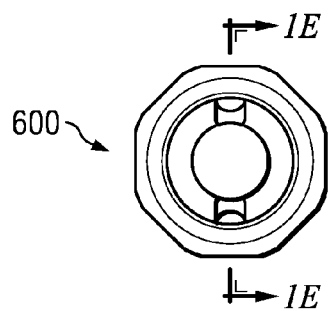
Figure 6E:
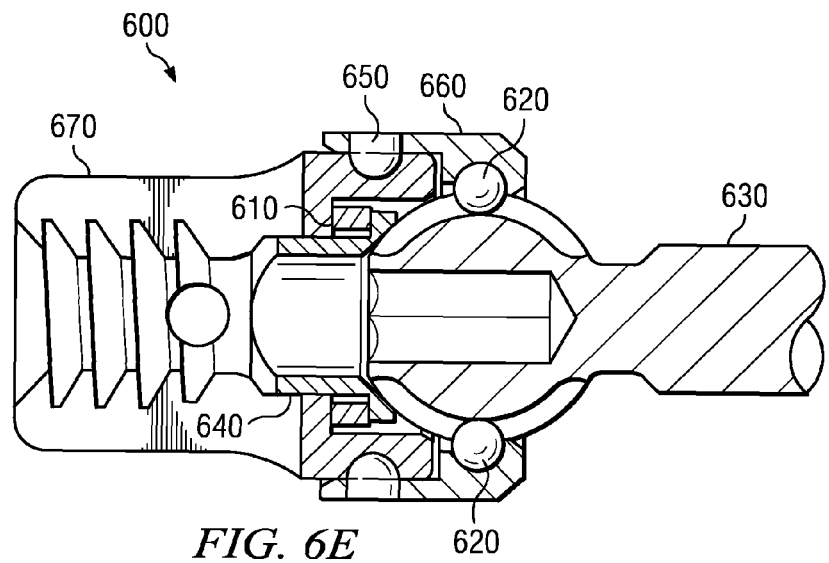
Figure 6F:
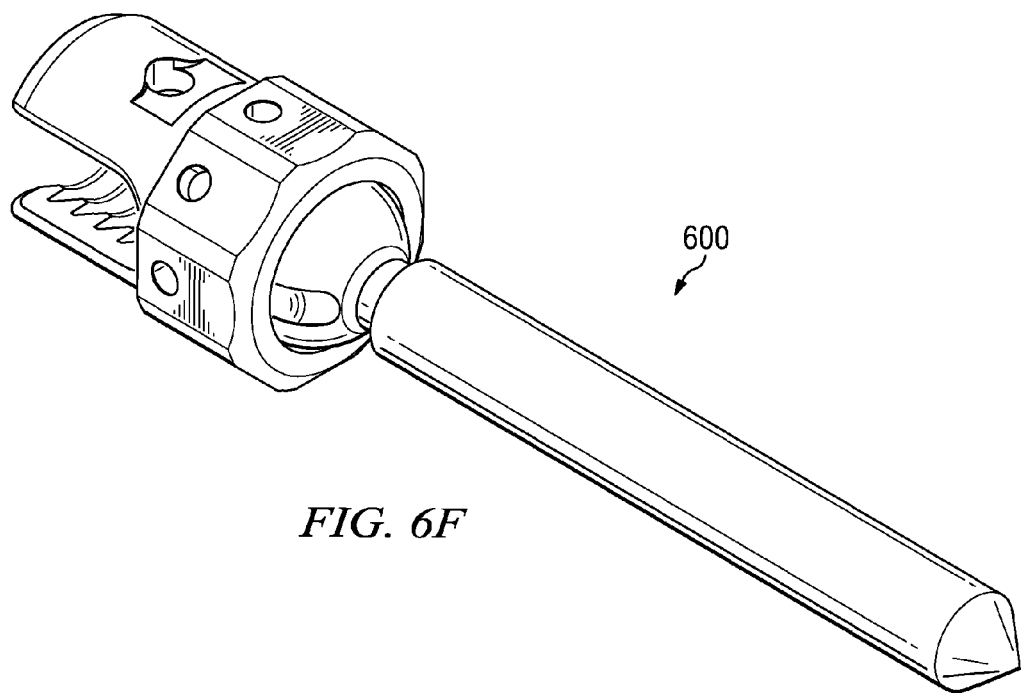

Various views of an exemplary embodiment of an implantable multi-axial pedicle fixation assembly 600 are illustrated in FIGS. 6A through 6F. Bone fixator 630 is angulatably connected to head assembly 680 such that the axis of bone fixator 630 may pivot relative to the axis of head assembly 680. Among other desirable benefits, this multi-axial feature maximizes range of motion and minimizes the need for extensive contouring of a spine stabilizing rod secured by head assembly 680, and also provides for simplified customization to accommodate variations in patient anatomy as well as variations in desired therapeutic benefits.

When the axis of bone fixator 630 and the axis of head assembly 680 are relatively aligned, such as during initial implantation, a primary drive interface may be used to adjust the depth at which bone fixator 630 penetrates the bone. The primary drive interface is located on bone fixator 630 and may be accessed with a tool inserted through head assembly 680.

Head assembly 680 comprises secondary drive component 660 and body component 670. Head assembly body component 670 is configured with a channel for receiving a spine stabilizing rod. Internal saddle member 640, for example a pressure cap, may nest within head assembly body component 670 and contact the stabilizing rod. When a stabilizing rod is secured within the channel of head assembly body component 670 with, for example, a setscrew or other such blocker, internal saddle member 640 transfers the received load to bone fixator 630, thus securing both the stabilizing rod and bone fixator 630 simultaneously. Wave spring 610 may place a pre-load upon the locking mechanism.

A secondary drive feature may operate similarly to a universal joint in that a kinematic linkage may be used to connect two angularly misaligned components, such as head assembly 680 and bone fixator 630. Since head assembly body component 670 is rotatably connected to head assembly secondary drive component 660 such that these components can rotate independently of one another, the rod-receiving channel of head assembly body component 670 may be independently repositioned while adjusting the depth at which bone fixator 630 penetrates the bone via the head assembly secondary drive component 660. Head assembly secondary drive component 660 may be cross-linked to bone fixator 630 via spherical drive balls 620. Spherical drive balls 620, which do not receive a locking load, traverse bone fixator 630 along elongated apertures, thus allowing multi-axial movement of head assembly 680 while transferring torsional loads to bone fixator 630. Such torsional loads adjust the depth at which bone fixator 630 penetrates the bone. The drive interface for head assembly secondary drive component 660 may be a square drive, a hex, a spline, a gear, or any other suitable drive interface, and may require the use of an external tool to adjust the depth of bone penetration.

Figure 7A:
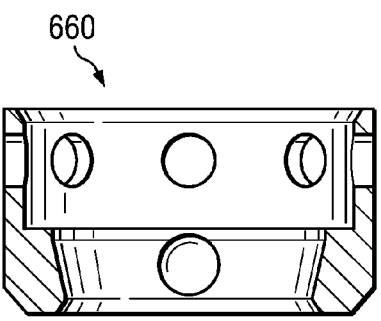
FIGS. 7A through 7D illustrate various views of an embodiment of a secondary drive component of a head assembly component of an implantable multi-axial pedicle fixation assembly.
Figure 7B:
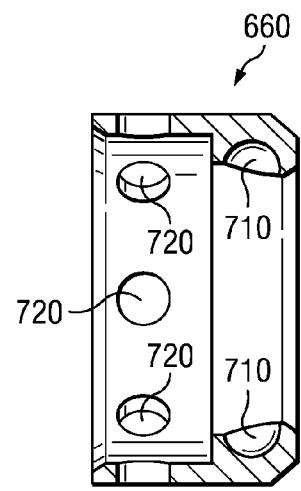
Figure 7C:
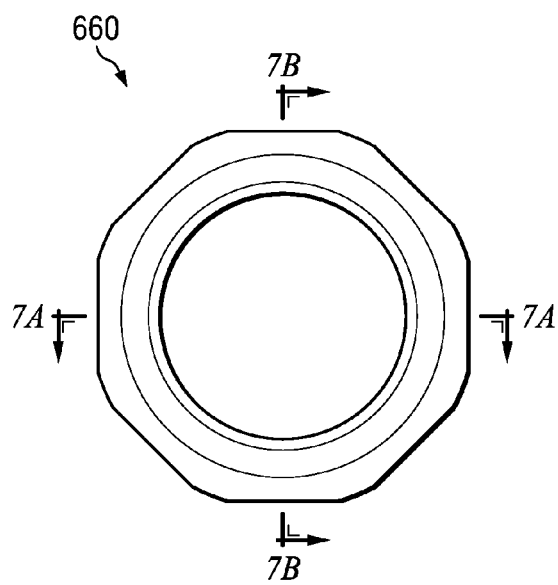
Figure 7D:
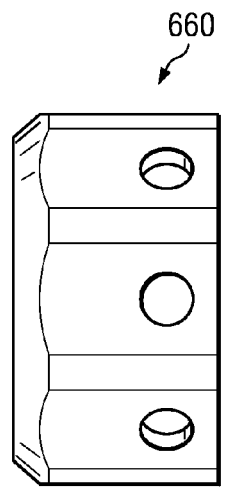
Figure 8A:
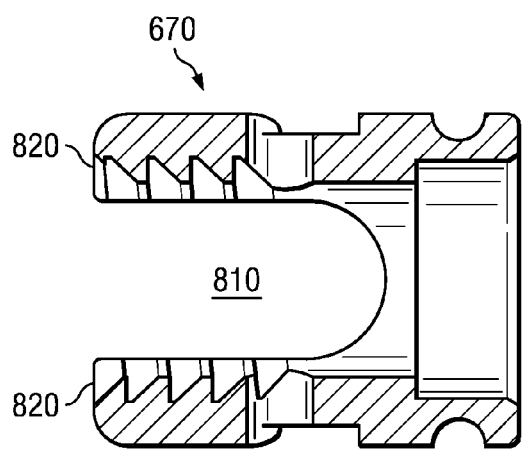
FIGS. 8A through 8H illustrate various views of an embodiment of a body component of a head assembly component of an implantable multi-axial pedicle fixation assembly.
Figure 8B:
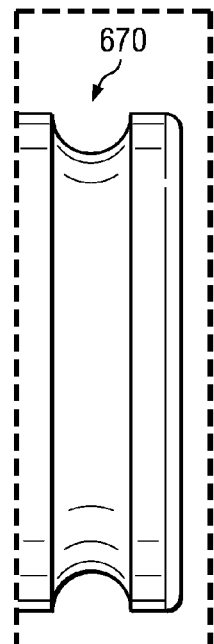
Figure 8C:
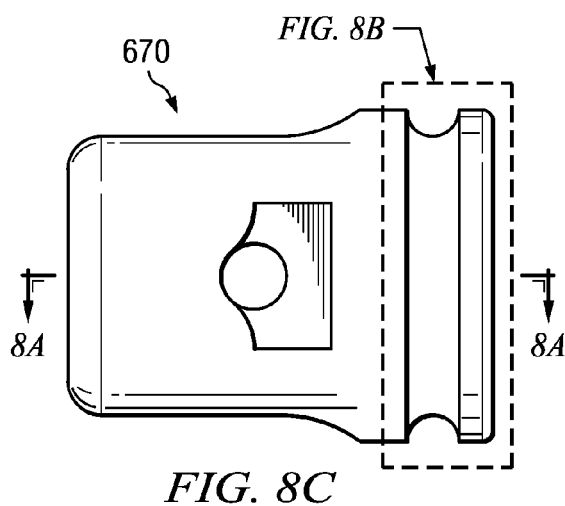
Figure 8D:
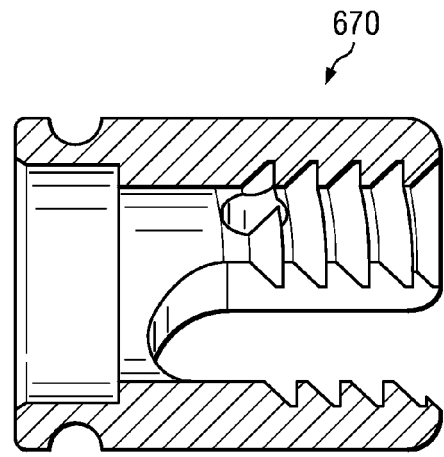
Figure 8E:
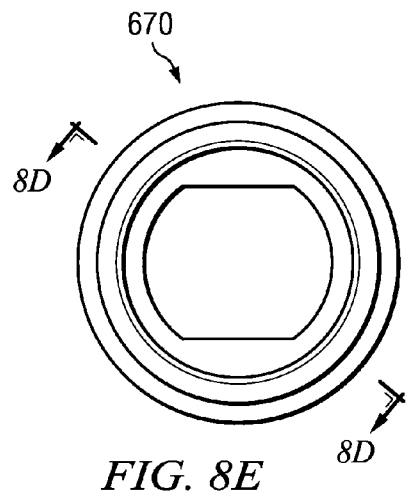
Figure 8F:
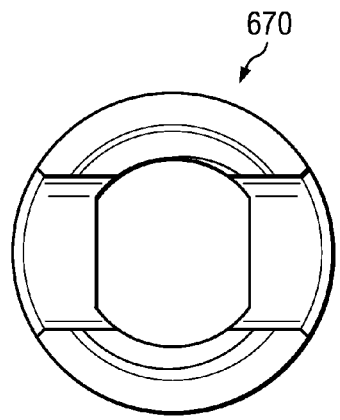
Figure 8G:
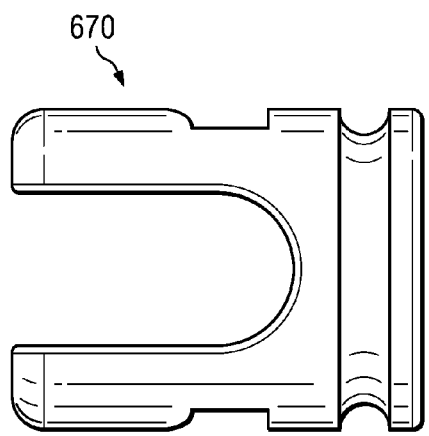
Figure 8H:
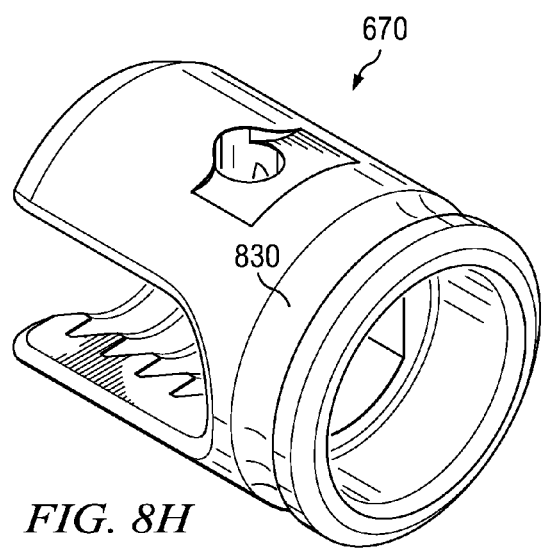

Various views of an exemplary embodiment of a head assembly secondary drive component 660 are illustrated in FIGS. 7A through 7D. Head assembly secondary drive component 660 comprises spherical drive ball receptacles 710 and fastening pin receptacles 720. Various views of an exemplary embodiment of a head assembly body component 670 are illustrated in FIGS. 8A through 8H. Head assembly body component 670 comprises rod-receiving channel 810, locking threads 820, and fastening pin channel 830. Locking threads 820 prevent the stabilizing rod from exiting channel 810, and in some embodiments a locking nut, locking cap, setscrew, or other component (not shown) may be employed to secure the stabilizing rod in channel 810. In some embodiments, head assembly 680 is still fully or partially adjustable after the introduction of the stabilizing rod but before the stabilizing rod is fully secured.

Looking now at FIGS. 6A through 6F, 7A through 7D, and 8A through 8H, to construct an embodiment of head assembly 680, spherical drive balls 620 are inserted into spherical drive ball receptacles 710. Bone fixator 630 is then inserted through head assembly drive component 660 such that spherical drive balls 620 rest within elongated apertures on bone fixator 630. Internal saddle member 640 and wave spring 610 may be positioned within a receptacle of head assembly body component 670. Body component 670 may then be united with secondary drive component 660. A fastening pin 650 may then be inserted into each fastening pin receptacle 720 such that fastening pin 650 contacts fastening pin channel 830. Fastening pins 650 may be welded, soldered, glued, or otherwise secured into fastening pin receptacle 720, thus securing together head assembly body component 670 and head assembly secondary drive component 660, while allowing the two components to freely rotate with respect to each other. Note that in alternate embodiments, the fastening pin channel may be located on the head assembly drive component, while the fastening pin receptacles may be located on the head assembly body component.

Figure 9A:
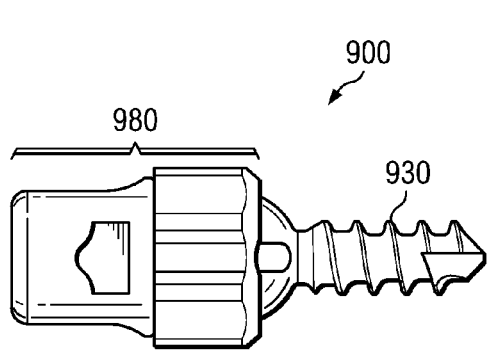
Figure 9B:
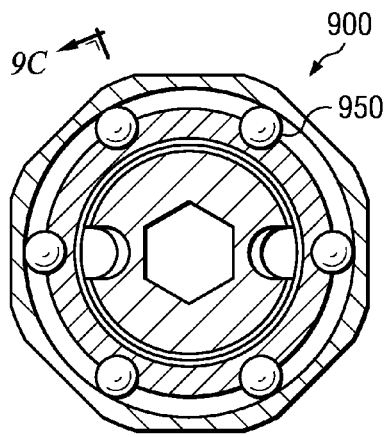
Figure 9C:
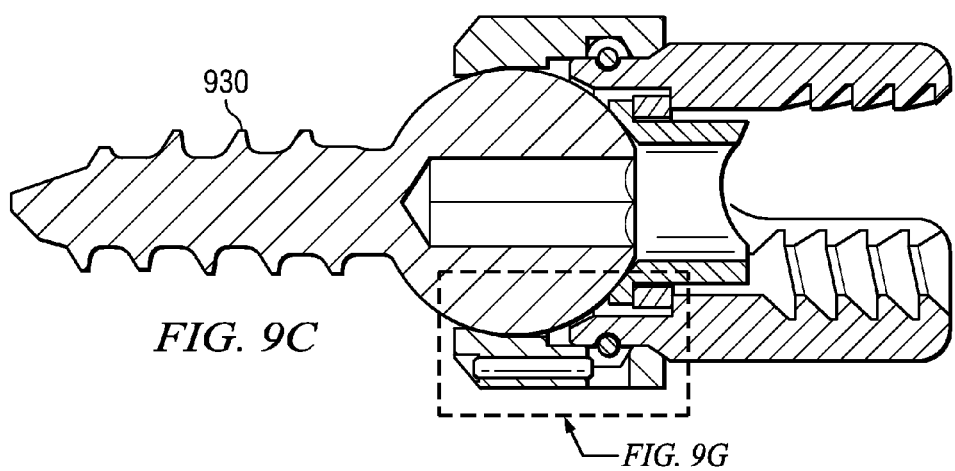
Figure 9D:
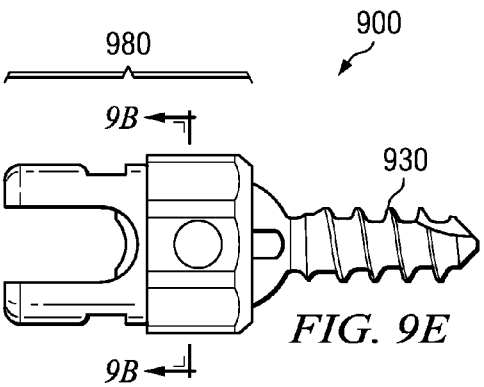
Figure 9E:
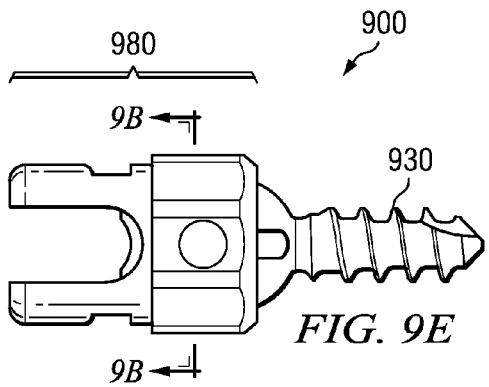

Various views of an exemplary embodiment of an implantable multi-axial pedicle fixation assembly 900 are illustrated in FIGS. 9A through 9I. Bone fixator 930 is angulatably connected to head assembly 980 such that the axis of bone fixator 930 may pivot relative to the axis of head assembly 980. Among other desirable benefits, this multi-axial feature maximizes range of motion and minimizes the need for extensive contouring of a spine stabilizing rod secured by head assembly 980, and also provides for simplified customization to accommodate variations in patient anatomy as well as variations in desired therapeutic benefits.

When the axis of bone fixator 930 and the axis of head assembly 980 are relatively aligned, such as during initial implantation, a primary drive interface may be used to adjust the depth at which bone fixator 930 penetrates the bone. The primary drive interface is located on bone fixator 930 and may be accessed with a tool inserted through head assembly 980.

Head assembly 980 comprises secondary drive component 960 and body component 970. Head assembly body component 970 is configured with a channel for receiving a spine stabilizing rod. Internal saddle member 940, for example a pressure cap, may nest within head assembly body component 970 and contact the stabilizing rod. When a stabilizing rod is secured within the channel of head assembly body component 970 with, for example, a setscrew or other such blocker, internal saddle member 940 transfers the received load to bone fixator 930, thus securing both the stabilizing rod and bone fixator 930 simultaneously. Wave spring 910 may place a pre-load upon the locking mechanism. Other embodiments may use a different system or no system for pre-loading the locking mechanism.

A secondary drive feature may operate similarly to a universal joint in that a kinematic linkage may be used to connect two angularly misaligned components, such as head assembly 980 and bone fixator 930. Since head assembly body component 970 is rotatably connected to head assembly secondary drive component 960 such that these components can rotate independently of one another, the rod-receiving channel of head assembly body component 970 may be independently repositioned while adjusting the depth at which bone fixator 930 penetrates the bone via the head assembly secondary drive component 960. Head assembly secondary drive component 960 may be cross-linked to bone fixator 930 via spherical drive balls 920. Spherical drive balls 920, which do not receive a locking load, traverse bone fixator 930 along elongated apertures, thus allowing multi-axial movement of head assembly 980 while transferring torsional loads to bone fixator 930. Such torsional loads adjust the depth at which bone fixator 930 penetrates the bone. In embodiments not shown, head assembly secondary drive component 960 may be cross-linked to bone fixator 930 via hinge pins or any other construct suitable to traverse bone fixator 930 along elongated apertures, thus allowing multi-axial movement of head assembly 980 while transferring torsional loads to bone fixator 930. The drive interface for head assembly secondary drive component 960 may be a square drive, a hex, a spline, a gear, or any other suitable drive interface, and may require the use of an external tool to adjust the depth of bone penetration.

Figure 10A:
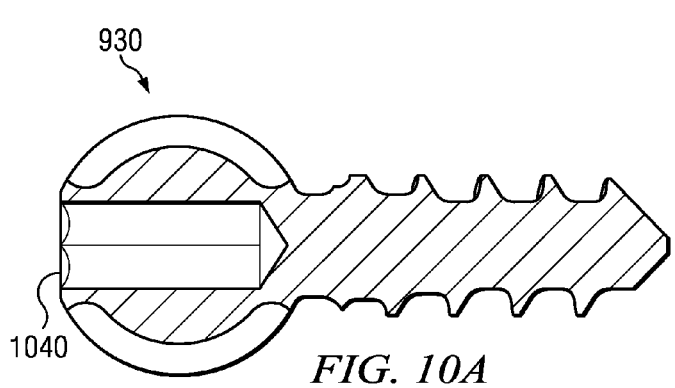
FIGS. 10A through 10F illustrate various views of an embodiment of a bone fixator component of an implantable multi-axial pedicle fixation assembly.
Figure 10B:
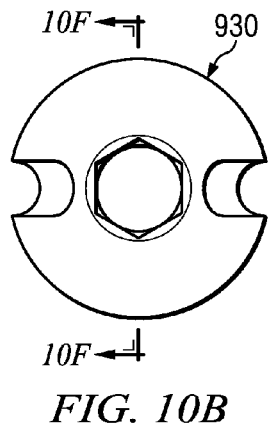
Figure 10C:
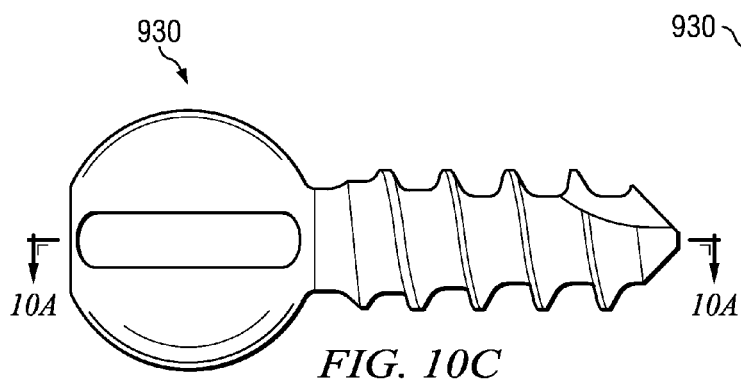
Figure 10D:
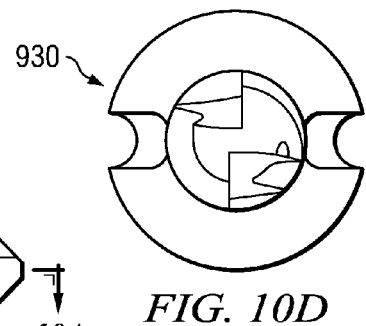
Figure 10E:
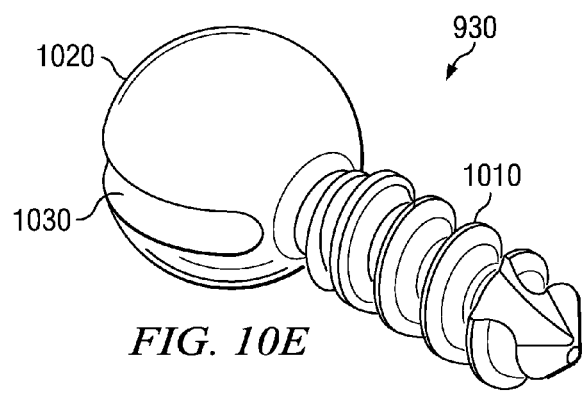
Figure 10F:
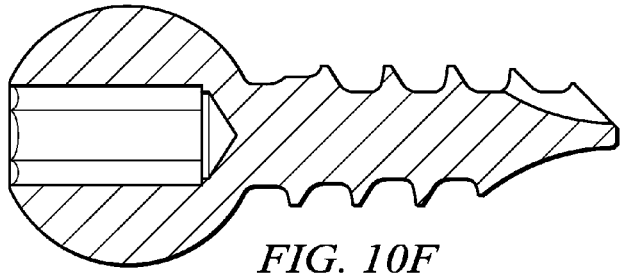

Various views of an exemplary embodiment of a bone fixator component 930 are illustrated in FIGS. 10A through 10F. Bone fixator 930 may be of any size and shape appropriate for penetrating a vertebral pedicle bone, may be solid, hollow, or a combination of solid and hollow, and may be made from any material suitable for implantation into the body, such as stainless steel, titanium, ceramic, or a composite material. Shaft 1010 may be smooth, or may be roughened, scored, or otherwise textured, and may generally be configured as a nail, a screw, a pin, or any other configuration suitable for bone fixation. Shaft 1010 may be cross-sectionally circular, polygonal, or any other shape suitable for bone fixation, and its bone-engaging terminus may be pointed, rounded, flattened, or otherwise shaped in a suitable manner for bone fixation. Knob 1020 may be integral with shaft 1010 or may be a separate component rigidly coupled to shaft 1010. The surface of knob 1020 may be spherical, and two elongated apertures 1030 may be diametrically opposed on either side of knob 1020. In this embodiment, elongated apertures 1030 are hemispherical blind apertures, such that spherical drive ball 920 (see FIG. 1) can roll smoothly along the aperture. In embodiments not shown, elongated apertures 1030 may be otherwise configured as long as spherical drive ball 920 can roll smoothly along the aperture. Primary drive interface 1040 is located on knob 1020 opposite shaft 1010. In the embodiment shown, primary drive interface 1040 is a hex screwdriver interface accessed with a tool (not shown), though other suitable primary drive interfaces are contemplated.

Figure 11A:
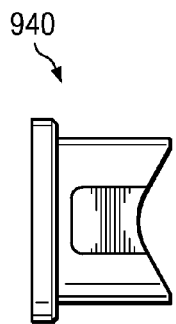
FIGS. 11A through 11E illustrate various views of an embodiment of an internal saddle member of an implantable multi-axial pedicle fixation assembly.
Figure 11B:
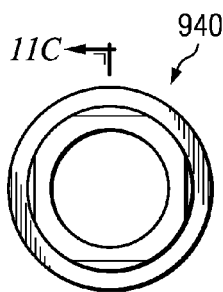
Figure 11C:
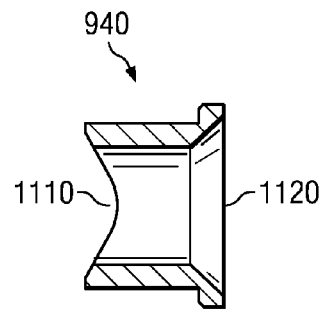
Figure 11D:
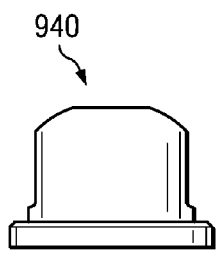
Figure 11E:
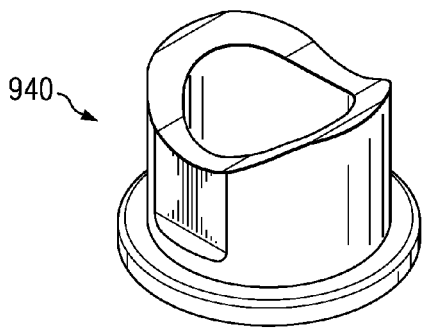

Various views of an exemplary embodiment of an internal saddle member 940 are illustrated in FIGS. 11A through 11E. Internal saddle member 940 may be positioned within a receptacle of head assembly body component 970 (see FIG. 1) such that rod-receiving channel 1110 aligns with the rod-receiving channel of head assembly body component 970. Internal saddle member 940 may be keyed to ensure alignment with rod-receiving channel 1110. Opening 1120 may be positioned to contact bone fixator 930 (see FIG. 1).

Figure 12A:
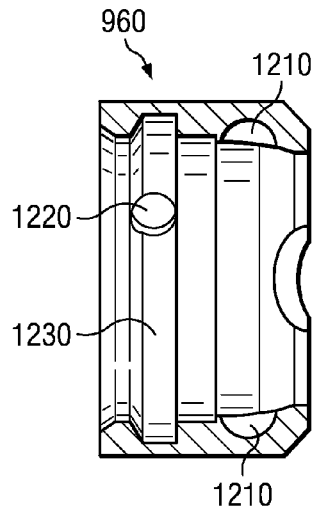
FIGS. 12A through 12G illustrate various views of an embodiment of a secondary drive component of a head assembly component of an implantable multi-axial pedicle fixation assembly.
Figure 12B:
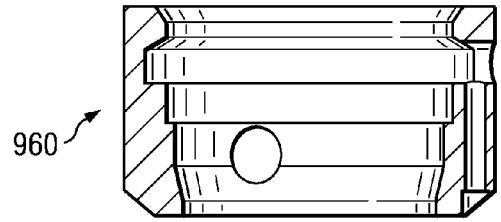
Figure 12C:
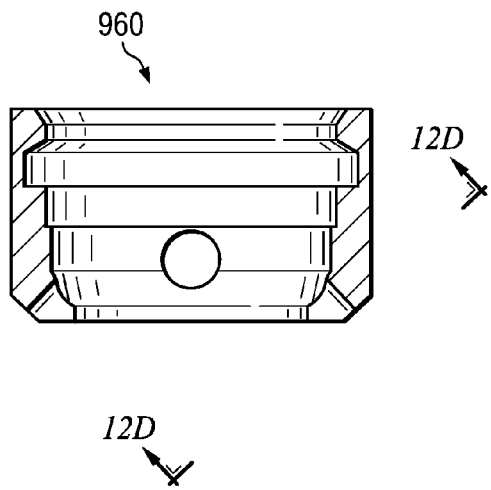
Figure 12D:
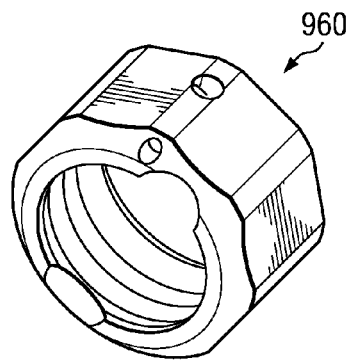
Figure 12E:
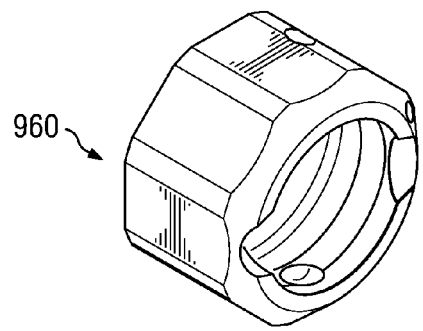
Figure 12F:
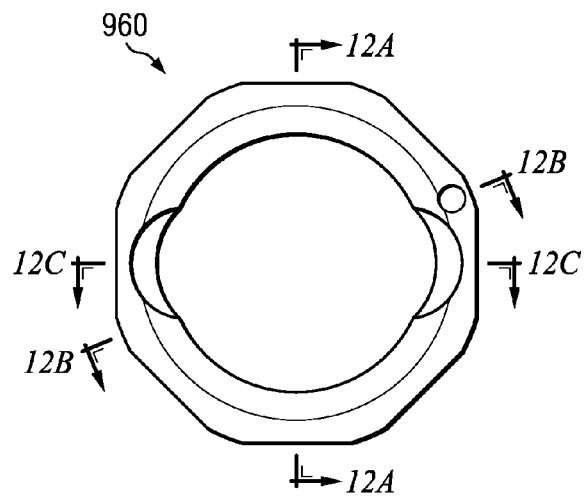
Figure 12G:
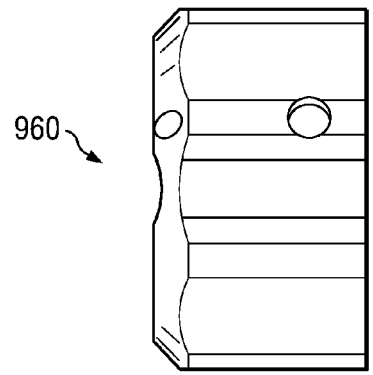
Figure 13A:
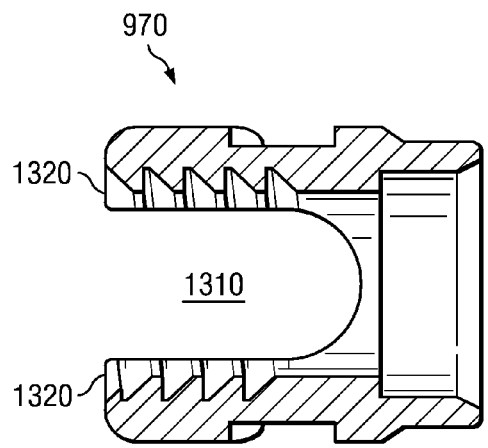
FIGS. 13A through 13I illustrate various views of an embodiment of a body component of a head assembly component of an implantable multi-axial pedicle fixation assembly.
Figure 13B:
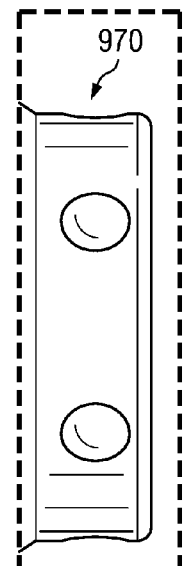
Figure 13C:
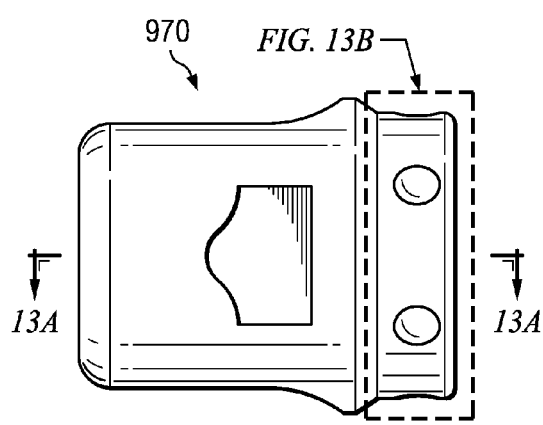
Figure 13D:
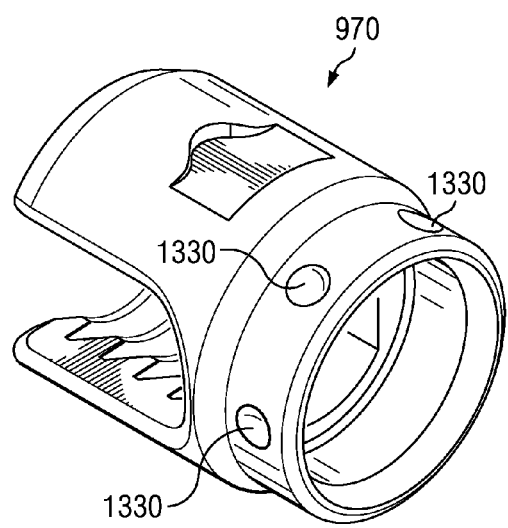
Figure 13E:
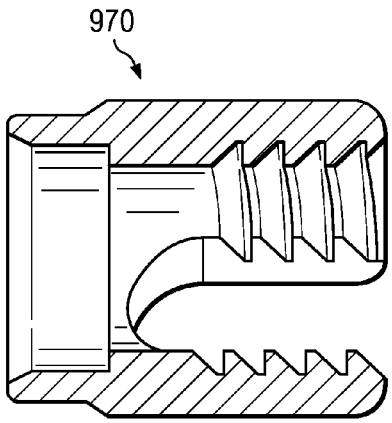
Figure 13F:
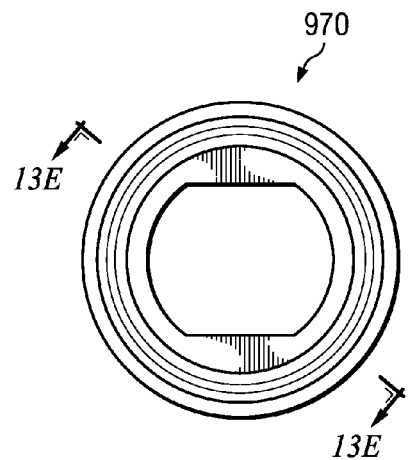
Figure 13G:
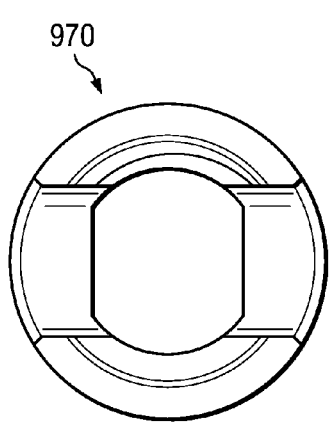
Figure 13H:
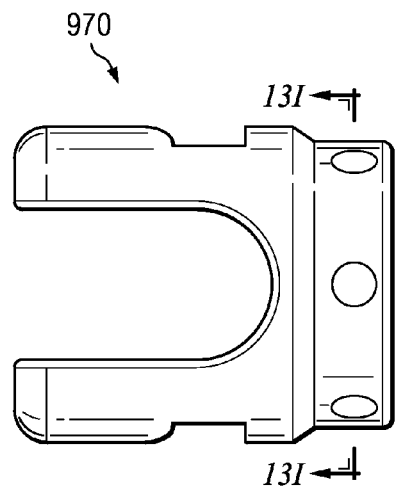
Figure 13I:
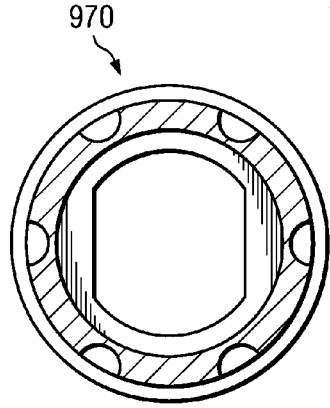

Various views of an exemplary embodiment of a head assembly secondary drive component 960 are illustrated in FIGS. 12A through 12G. Head assembly secondary drive component 960 comprises spherical drive ball receptacles 1210 and opening 1220 into fastening ball channel 1230. Various views of an exemplary embodiment of a head assembly body component 970 are illustrated in FIGS. 13A through 13I. Head assembly body component 970 comprises rod-receiving channel 1310, locking threads 1320, and fastening ball dimples 1330. Locking threads 1320 prevent the stabilizing rod from exiting channel 1310, and in some embodiments a locking nut, locking cap, setscrew, or other component (not shown) may be employed to secure the stabilizing rod in channel 1310. In some embodiments, head assembly 980 is still fully or partially adjustable after the introduction of the stabilizing rod but before the stabilizing rod is fully secured.

Looking now at FIGS. 9A through 9H, 10A through 10F, 11A through 11E, 12A through 12G, and 13A through 13I, to construct an embodiment of head assembly 980, spherical drive balls 920 are inserted into spherical drive ball receptacles 1210. Bone fixator 930 is then inserted through head assembly drive component 960 such that spherical drive balls 920 rest within elongated apertures 1030. Internal saddle member 940 and wave spring 910 may be positioned within a receptacle of head assembly body component 970. Body component 970 may then be united with secondary drive component 960. Fastening ball dimple 1330 may then be aligned with opening 1220 of head assembly secondary drive component 960 for insertion of fastening ball 950 into fastening ball channel 1230. Body component 970 may then be rotated until the next fastening ball dimple 1330 is aligned with opening 1220 for insertion of another fastening ball 950 until each fastening ball dimple 1330 is occupied by fastening ball 950, thus securing together head assembly body component 970 and head assembly secondary drive component 960, while allowing the two components to freely rotate with respect to each other. Note that in alternate embodiments, the fastening ball channel may be located on the head assembly body component, while the fastening ball dimples may be located on the head assembly drive component.

Although the present invention has been described in detail, it should be understood that various changes, substitutions, and alterations can be made without departing from the spirit and scope of the invention as defined by the appended claims. In particular, various features from the described embodiments may be recombined in various ways to produce alternate embodiments. Various terms used herein have special meanings within the present technical field. Whether a particular term should be construed as such a "term of art" depends on the context in which that term is used. "Connected to," "coupled to," "secured to," "in contact with," or other similar terms should generally be construed broadly. These and other terms are to be construed in light of the context in which they are used in the present disclosure and as those terms would be understood by one of ordinary skill in the art would understand those terms in the disclosed context. The above definitions are not exclusive of other meanings that might be imparted to those terms based on the disclosed context.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

We claim:

1. A fixation device comprising:
   a bone fixator having a longitudinal axis and proximal and distal ends, the distal end including an outer surface adapted to penetrate and anchor within bone;
   a body component adapted to receive a stabilizing rod and having an outer surface comprising at least one dimple operable to receive a corresponding fastening ball;
   a drive component connected to the body component and having a longitudinal axis, an outer surface operable to connect to a driving tool, and an inner surface comprising a channel receiving at least one fastening ball, wherein the at least one fastening ball is positioned between the channel of the inner surface of the drive component and the at least one dimple of the outer surface of the body component so that the body component is independently rotatable with respect to the drive component; and
   at least one cross-link connecting the drive component to the proximal end of the bone fixator such that when the drive component is rotated about its longitudinal axis, a torsional load is transferred to the bone fixator while the longitudinal axis of the drive component is not parallel to a longitudinal axis of the bone fixator, and wherein the longitudinal axis of the bone fixator is pivotable relative to the longitudinal axis of the drive component while secured thereto.

2. A fixation device according to claim 1, further comprising:
   a saddle member having a proximal end and an distal end, wherein the saddle member is disposed within the body component;
   wherein the distal end of the saddle member comprises a surface for engaging the proximal end of the bone fixator;
   wherein the proximal end of the saddle member comprises a surface for engaging the stabilizing rod;
   wherein the saddle member is operable to maintain a fixed axial position within the body component while the drive component is actuated to rotate the bone fixator.

3. A fixation device according to claim 2 wherein the distal end of the saddle member further comprises an external annular lip and the body member further comprises an internal annular lip, and
    wherein the fixation device further comprises a loading device positioned between the annular lip of the saddle member and the annular lip of the body component, wherein the loading device maintains an engagement between the surface at the distal end of the saddle member and the proximal end of the bone fixator.

4. A fixation device according to claim 3, wherein the loading device comprises a wave spring.

5. A fixation device according to claim 2,
    wherein the distal end of the saddle member is further operable to maintain engagement with the proximal end of the bone fixator while the drive component is actuated.

6. A fixation device according to claim 2 wherein the application of a load by the stabilizing rod against the proximal end of the saddle member causes a load to be applied by the distal end of the saddle member against the proximal end of the bone fixator.

7. A fixation device according to claim 1, wherein the proximal end of the bone fixator comprises a substantially spherical surface that includes at least one elongated aperture aligned with the longitudinal axis of the bone fixator;
    wherein an interior surface of the drive component comprises at least one dimple corresponding to the at least one elongated aperture; and
    wherein the cross-link comprises a ball that is disposed in the elongated aperture of the bone fixator and in the corresponding dimple in the drive component such that when the drive component is articulated with respect to the bone fixator, the ball travels within the elongated aperture while remaining within the corresponding dimple.

8. A fixation device according to claim 7, wherein the proximal end of the bone fixator comprises two elongated apertures positioned on opposite sides of the substantially spherical surface;
    wherein the interior surface of the drive component comprises two dimples positioned on opposite sides of the interior surface; and
    wherein the cross-link comprises two balls that are disposed in the elongated apertures and the corresponding dimples.

9. A fixation device according to claim 1, wherein the outer surface of the drive component comprises a hexagonal surface.

10. A fixation device comprising:
    a bone fixator having a longitudinal axis and proximal and distal ends, the distal end including an outer surface adapted to penetrate and anchor within bone;
    a body component having a proximal and distal ends, wherein the body component is adapted to receive a stabilizing rod at the proximal end, and wherein the distal end of the body component comprises an outer surface comprising at least one dimple operable to receive a corresponding fastening ball;
    a drive component connected to the body component, having a longitudinal axis and proximal and distal ends, and comprising an outer surface operable to connect to a driving tool and, at the proximal end, an inner surface comprising a channel receiving at least one fastening ball, wherein the at least one fastening ball is positioned between the channel of the inner surface of the drive component and the at least one dimple of the outer surface of the body component so that the body component is independently rotatable with respect to the drive component; and
    at least one cross-link connecting the drive component to the proximal end of the bone fixator such that when the drive component is rotated about its longitudinal axis, a torsional load is transferred to the bone fixator while the longitudinal axis of the drive component is not parallel to a longitudinal axis of the bone fixator, and wherein the longitudinal axis of the bone fixator is pivotable relative to the longitudinal axis of the drive component while secured thereto.

11. A fixation device according to claim 10, further comprising:
    a saddle member having a proximal end and an distal end, wherein the saddle member is disposed within the body component;
    wherein the distal end of the saddle member comprises a surface for engaging the proximal end of the bone fixator;
    wherein the proximal end of the saddle member comprises a surface for engaging the stabilizing rod;
    wherein the saddle member is operable to maintain a fixed axial position within the body component while the drive component is actuated to rotate the bone fixator.

12. A fixation device according to claim 11 wherein the distal end of the saddle member further comprises an external annular lip and the body member further comprises an internal annular lip, and
    wherein the fixation device further comprises a loading device positioned between the annular lip of the saddle member and the annular lip of the body component, wherein the loading device maintains an engagement between the surface at the distal end of the saddle member and the proximal end of the bone fixator.

13. A fixation device according to claim 12, wherein the loading device comprises a wave spring.

14. A fixation device according to claim 11, wherein the proximal end of the bone fixator comprises a substantially spherical surface that includes at least one elongated aperture aligned with the longitudinal axis of the bone fixator;
    wherein an interior surface of the drive component comprises at least one dimple corresponding to the at least one elongated aperture; and
    wherein the cross-link comprises a ball that is disposed in the elongated aperture of the bone fixator and in the corresponding dimple in the drive component such that when the drive component is articulated with respect to the bone fixator, the ball travels within the elongated aperture while remaining within the corresponding dimple.

15. A fixation device according to claim 14, wherein the proximal end of the bone fixator comprises two elongated apertures positioned on opposite sides of the substantially spherical surface;
    wherein the interior surface of the drive component comprises two dimples positioned on opposite sides of the interior surface; and
    wherein the cross-link comprises two balls that are disposed in the elongated apertures and in the corresponding dimples.

16. A fixation device according to claim 11,
    wherein the distal end of the saddle member is further operable to maintain engagement with the proximal end of the bone fixator while the drive component is actuated.

17. A fixation device according to claim 11 wherein the application of a load by the stabilizing rod against the proximal end of the saddle member causes a load to be applied by the distal end of the saddle member against the proximal end of the bone fixator.

18. A fixation device according to claim 10, wherein the drive component further comprises an opening passing from an outer surface of the drive component to the channel and is sized to receive a fastening ball when the dimple on the outside surface of the body component is aligned with the opening.

19. A fixation device according to claim 10, wherein
the distal end of the body component further comprises an outer cylindrical surface with a fastening pin channel operable to receive at least one fastening pin;
the proximal end of the drive component further comprises at least one receptacle operable to receive a corresponding fastening pin; and
at least one fastening pin that is positioned between the body component and the drive component and promotes rotational movement of the body component with respect to the drive component.

* * * * *